(12) United States Patent
Umihira et al.

(10) Patent No.: US 11,733,130 B2
(45) Date of Patent: Aug. 22, 2023

(54) TISSUE DIVIDING JIG

(71) Applicants: Umihira Co., Ltd., Kyoto (JP); Kyoto Prefectural Public University Corporation, Kyoto (JP)

(72) Inventors: Kazuo Umihira, Kyoto (JP); Keizou Ogino, Kyoto (JP); Osamu Ukimura, Kyoto (JP); Kazumi Kamoi, Kyoto (JP)

(73) Assignees: Umihira Co., Ltd., Kyoto (JP); Kyoto Prefectural Public University Corporation, Kyoto (JP)

( * ) Notice: Subject to any disclaimer, the term of this patent is extended or adjusted under 35 U.S.C. 154(b) by 1056 days.

(21) Appl. No.: 16/310,842

(22) PCT Filed: Oct. 5, 2017

(86) PCT No.: PCT/JP2017/036333
§ 371 (c)(1),
(2) Date: Dec. 18, 2018

(87) PCT Pub. No.: WO2018/066658
PCT Pub. Date: Apr. 12, 2018

(65) Prior Publication Data
US 2019/0178757 A1    Jun. 13, 2019

(30) Foreign Application Priority Data

Oct. 7, 2016  (JP) ................. 2016-198959

(51) Int. Cl.
*G01N 1/04*    (2006.01)
*G01N 1/28*    (2006.01)
(Continued)

(52) U.S. Cl.
CPC ............... *G01N 1/04* (2013.01); *A61B 10/02* (2013.01); *A61B 10/0233* (2013.01);
(Continued)

(58) Field of Classification Search
None
See application file for complete search history.

(56) References Cited

U.S. PATENT DOCUMENTS 5,612,218 A    3/1997  Busch et al.
6,451,262 B1 * 9/2002  Chiodo ................ G01N 1/2813
                                                    83/651.1
(Continued)

FOREIGN PATENT DOCUMENTS

JP    2000-210892 A    8/2000
JP    2004-28985 A     1/2004
(Continued)

OTHER PUBLICATIONS

The Extended European Search Report dated Apr. 20, 2020, of counterpart European Application No. 17858494.2.

*Primary Examiner* — Benjamin S Melhus
(74) *Attorney, Agent, or Firm* — DLA Piper LLP (US)

(57) ABSTRACT

A tissue dividing jig includes a tissue dividing base; and a cutting blade set provided with a cutting blade member and a guide portion, the tissue dividing base and the cutting blade set have a positioning mechanism that fixes their positions mutually, the cutting blade member is provided with a cutting blade extending in a longitudinal direction of the tissue placement portion, the guide portion guides the cutting blade member to move the cutting blade member to a fixed position on the tissue dividing base, and the cutting blade is disposed such that when the cutting blade set is disposed at a predetermined position on the tissue dividing base by the positioning mechanism and the cutting blade member is moved using the guide portion, the cutting blade divides the needle biopsy tissue on the tissue placement portion in the longitudinal direction.

1 Claim, 8 Drawing Sheets

(51) Int. Cl.
*A61B 10/02* (2006.01)
*G01N 1/06* (2006.01)

(52) U.S. Cl.
CPC ........... *A61B 10/0275* (2013.01); *G01N 1/06* (2013.01); *G01N 1/28* (2013.01); *G01N 2001/061* (2013.01)

(56) References Cited

U.S. PATENT DOCUMENTS

| | | | |
|---|---|---|---|
| 7,393,685 B1 | 7/2008 | Jordan | |
| 7,673,545 B1* | 3/2010 | Giberson | B26D 1/15 83/881 |
| 8,191,453 B2* | 6/2012 | Ichihara | G01N 1/06 83/522.19 |
| 9,097,619 B2* | 8/2015 | Ichihara | G01N 1/06 |
| 9,341,551 B2* | 5/2016 | Pasternak | A61B 10/0266 |
| 2003/0198574 A1* | 10/2003 | Studer | G02B 21/34 422/536 |
| 2004/0175820 A1* | 9/2004 | Shigematsu | G01N 1/06 435/287.1 |
| 2005/0095666 A1* | 5/2005 | Jhavar | A61B 17/3211 435/40.52 |
| 2006/0106378 A1* | 5/2006 | Kobayashi | A61B 17/32 606/45 |
| 2008/0227144 A1* | 9/2008 | Nightingale | G01N 1/312 435/40.52 |
| 2009/0293689 A1* | 12/2009 | Ichihara | G01N 1/06 83/34 |
| 2010/0050838 A1* | 3/2010 | Noguchi | G01N 1/36 83/762 |
| 2010/0076473 A1* | 3/2010 | Tawfik | G01N 1/06 606/167 |
| 2010/0184127 A1* | 7/2010 | Williamson, IV | B01L 9/52 435/40.52 |
| 2011/0008884 A1* | 1/2011 | Morales | G01N 1/06 435/325 |
| 2011/0282239 A1* | 11/2011 | Conlon | A61B 10/0275 128/898 |
| 2014/0234895 A1* | 8/2014 | Morales | G01N 1/36 435/40.52 |
| 2014/0377148 A1* | 12/2014 | Pasternak | G01N 33/4833 422/561 |
| 2015/0238173 A1* | 8/2015 | Wegener | A61B 10/0275 600/566 |
| 2018/0348097 A1* | 12/2018 | Abbott | G01N 1/286 |

FOREIGN PATENT DOCUMENTS

| | | |
|---|---|---|
| JP | 2011-500285 A | 1/2011 |
| JP | 2012-220280 A | 11/2012 |
| JP | 2016-505841 A | 2/2016 |
| JP | 2017-003504 A | 1/2017 |
| KR | 10-2013-0045465 A | 5/2013 |
| WO | 2009/055640 A1 | 4/2009 |
| WO | 2010/130974 A2 | 11/2010 |
| WO | 2014/097295 A1 | 6/2014 |

* cited by examiner

TISSUE DIVIDING JIG

TECHNICAL FIELD

This disclosure relates to a tissue dividing jig.

BACKGROUND

Biopsies are essential means for accurately diagnosing diseases. Most commonly, biopsies are performed with the use of a biopsy gun. When the biopsy gun is used, one or more needles are moved forward in a target tissue typically under ultrasonic guidance or MRI guidance. Next, a tissue fragment (core) is taken out together with the biopsy needle(s). The tissue fragment is collected from the needle(s), and then immersed in a fixing agent (formalin fixation) or frozen. Subsequently, the tissue fragment is embedded in paraffin, sliced, and subjected to frozen segmentation. The tissue fragment is then placed on a microscope slide, and subjected to coloring, nucleic acid analysis, or other analyses. In many cases, process steps for visual analyses of the tissue fragment (such as a treatment with a fixing agent, paraffin embedding, coloring and the like) are incompatible with process steps for molecular biological analyses of the tissue fragment (in situ PCR, fluorescent in situ hybridization and the like). Accordingly, it is necessary to collect many needle biopsy tissues from a site being examined.

For example, in prostate biopsy, tissue fragments are collected by transperineal or transrectal needle biopsy. Thus, elongated columnar fragments are collected. To minimize the risk of bleeding, infection and the like accompanying the prostate biopsy, it is desirable that the number of tissue fragments to be collected is as few as possible. On the other hand, since it is technically impossible to perform sampling twice on the same site, large-scale DNA analysis for prostate cancer utilizing biopsy tissues has not been performed. On this account, there has been proposed a tissue dividing biopsy needle that includes a needle portion and a sheath portion so that it can divide a tissue (see Japanese Translation of PCT International Application Publication No. JP-T-2011-500285, for example).

However, when tissue is divided inside a biopsy needle, the tissue may slip inside the biopsy needle or, when taking out tissue fragments from the biopsy needle after dividing the tissue, the tissue fragments may be deformed or compressed, resulting in misalignment of the tissue fragments. Also, it is difficult to control dividing positions of the tissue. To avoid such drawbacks, it is conceivable to divide the biopsy tissue after being collected from the needle and before being processed. However, such division after collecting the biopsy tissue requires fairly expert skill and equipment that is not generally available in clinics where biopsies are performed. Furthermore, even if extreme care is taken to divide the biopsy tissue evenly, it is difficult to perform consistent division over the entire length of the core.

With the foregoing in mind, it could be helpful to provide a tissue dividing jig that can easily divide a needle biopsy tissue to be subjected to biopsy into a plurality of fragments, namely, two fragments or three or more fragments over the entire length of the needle biopsy tissue, thereby allowing divided tissues with spatial correspondence to be obtained.

SUMMARY

We provide a tissue dividing jig for dividing a needle biopsy tissue in a longitudinal direction, including: a tissue dividing base; and a cutting blade set, wherein the tissue dividing base has a tissue placement portion on which the needle biopsy tissue is to be placed, the cutting blade set is provided with a cutting blade member and a guide portion, the tissue dividing base and the cutting blade set have a positioning mechanism that fixes their positions mutually, the cutting blade member is provided with a cutting blade that extends in a longitudinal direction of the tissue placement portion, the guide portion guides the cutting blade member to move the cutting blade member to a fixed position on the tissue dividing base, and when the cutting blade set is disposed at a predetermined position on the tissue dividing base by the positioning mechanism and the cutting blade member is moved using the guide portion, the cutting blade is disposed at a position where the cutting blade divides the needle biopsy tissue placed on the tissue placement portion in the longitudinal direction.

We also provides a tissue dividing jig for dividing a needle biopsy tissue in a longitudinal direction, including: a tissue dividing base; and a cutting blade set, wherein the tissue dividing base has a tissue placement portion on which the needle biopsy tissue is to be placed, the cutting blade set is provided with a cutting blade member and a guide portion, the tissue dividing base and the cutting blade set have a positioning mechanism that fixes their positions mutually, the cutting blade member is provided with a cutting blade that extends in a longitudinal direction of the tissue placement portion, the guide portion guides the cutting blade member to move the cutting blade member to a fixed position on the tissue dividing base, and when the cutting blade set is disposed at a predetermined position on the tissue dividing base by the positioning mechanism and the cutting blade member is moved using the guide portion, the cutting blade is disposed at a position where the cutting blade divides the needle biopsy tissue placed on the tissue placement portion into two fragments in the longitudinal direction.

It is preferable that a sheet-like member having an affinity for the needle biopsy tissue is further placed on the tissue placement portion.

It is preferable that that the sheet-like member can be divided with the cutting blade.

It is preferable that the tissue dividing base can be divided at a cutting position of the needle biopsy tissue.

The tissue dividing jig preferably further includes a biopsy needle guide that can fix a biopsy needle carrying the needle biopsy tissue collected therewith in a lengthwise direction.

We thus provide a tissue dividing jig that can easily divide a needle biopsy tissue to be subjected to a biopsy into a plurality of fragments, namely, two fragments or three or more fragments over the entire length of the needle biopsy tissue, thereby allowing divided tissues with spatial correspondence to be obtained.

Figure 1:
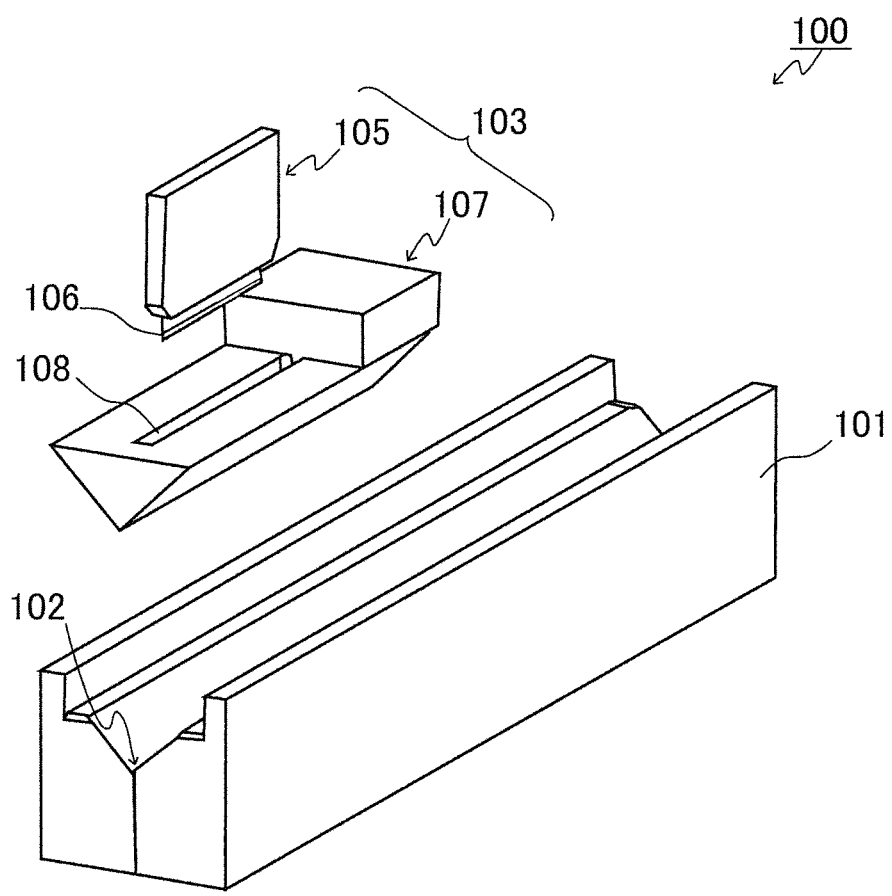
FIG. 1 is an exploded perspective view showing a tissue dividing jig 100 according to a first example.

REFERENCE SIGNS LIST 100, 200, 300: Tissue dividing jig
101, 101A, 101B, 201, 201A, 201B, 301: Tissue dividing base
102, 202, 302: Tissue placement portion
103, 203, 303: Cutting blade set
105, 205, 305: Cutting blade member
106, 206, 306: Cutting blade
107: Guide portion
108: Guide hole
109, 209, 309: Sheet-like member
120: Biopsy needle
121: Notch
207: Guide portion (positioning mechanism)
210: Positioning pin (positioning mechanism)
215, 315: Pressing member
216: Positioning hole
220, 220A, 221, 321: Biopsy needle guide
230: Biopsy needle stopper portion (biopsy needle stopper wall)
307: Hinge (guide portion, positioning mechanism)
316: Hinge
330: Button
S, SA, SB: Needle biopsy tissue

DETAILED DESCRIPTION

Our tissue dividing jigs will be described with reference to illustrative examples. It is to be noted, however, that this disclosure is not limited to or restricted by the following examples.

FIRST EXAMPLE

Figure 2:
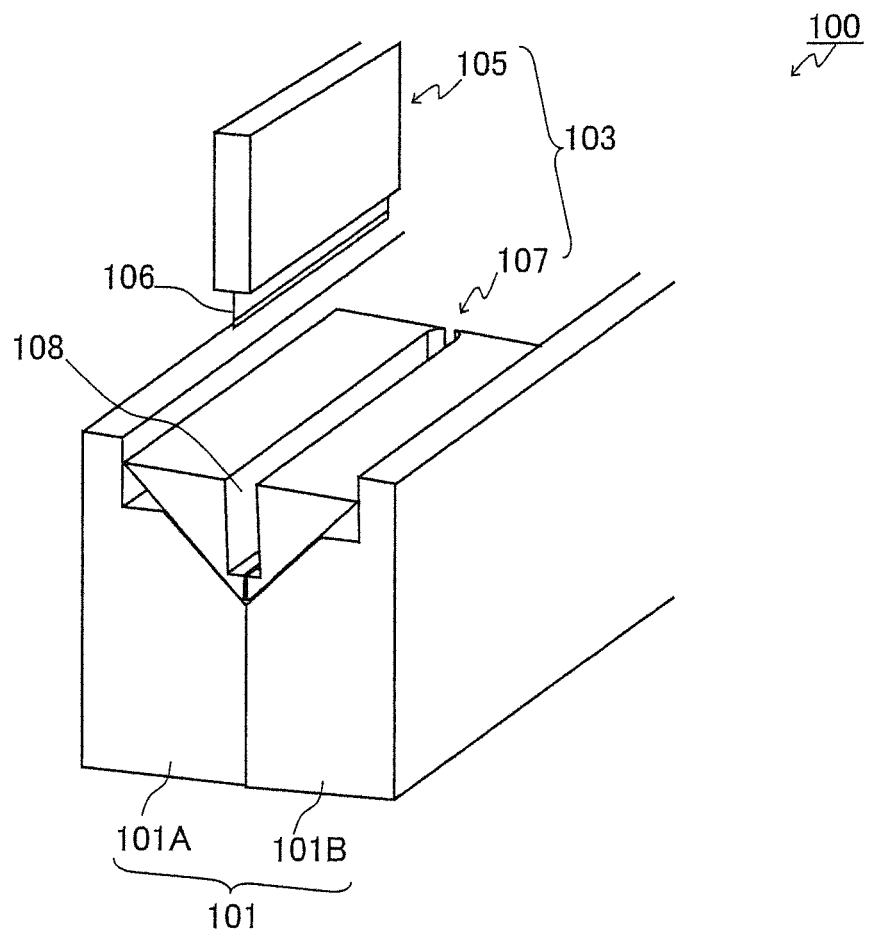
FIG. 2 is a perspective view showing the state of the tissue dividing jig 100 at the time of dividing a needle biopsy tissue.
Figure 3:
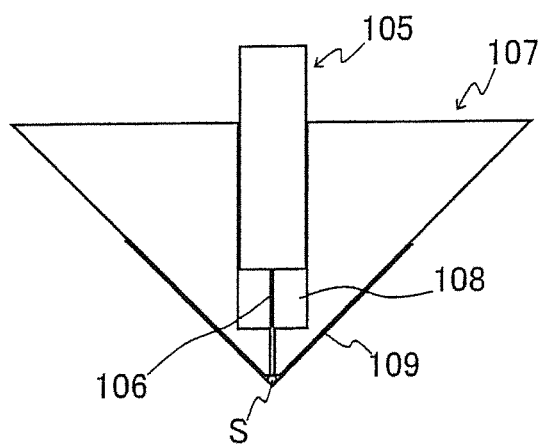
FIG. 3 is a partially enlarged sectional view of the tissue dividing jig 100 at the time of dividing a needle biopsy tissue.

FIGS. 1 and 2 show a tissue dividing jig 100 according to a first example. FIG. 1 is an exploded perspective view, and FIG. 2 is a perspective view showing the state of the tissue dividing jig 100 at the time of dividing a needle biopsy tissue. FIG. 3 is a partially enlarged sectional view of the tissue dividing jig 100 at the time of dividing a needle biopsy tissue S. The tissue dividing jig 100 has a tissue dividing base 101 and a cutting blade set 103. The tissue dividing base 101 has a tissue placement portion 102 on which a needle biopsy tissue is to be placed. The cutting blade set 103 is provided with a cutting blade member 105 and a guide portion 107.

The tissue dividing base 101 and the cutting blade set 103 have a positioning mechanism that fixes their positions mutually. The positioning mechanism in this example is such that the tissue dividing base 101 and the guide portion 107 have cross-sectional shapes that can be combined with each other to fix the tissue dividing base 101 and the guide portion 107. That is, the cross section of the tissue dividing base 101 is in a shape of a V-shaped notch, and the cross section of the guide portion 107 is in a shape that fits into the cross section of the tissue dividing base 101 when combined with the tissue dividing base 101 (i.e., a triangular shape with a vertex having substantially the same angle as the angle of the V-shaped notch), whereby the positioning of the tissue dividing base 101 and the cutting blade set 103 is achieved. The guide portion 107 has a guide hole 108 that moves the cutting blade member 105 to a fixed position.

The cutting blade member 105 is provided with a cutting blade 106 that extends in the longitudinal direction of the tissue placement portion 102. The cutting blade 106 is disposed at a position where, when the guide portion 107 is disposed at the predetermined position on the tissue dividing base 101 by the positioning mechanism and the cutting blade member 105 is moved along the guide hole 108, the cutting blade 106 divides the needle biopsy tissue S placed on the tissue placement portion 102 into two fragments in the longitudinal direction.

In a large tumor in a large organ, it is possible to collect many needle biopsy tissues from the same site. However, in prostate cancer or the like in which malignant tumors are relatively small and distributed irregularly in the organ, a plurality of collected needle biopsy tissues do not exhibit exactly the same properties (e.g., the proportion of the malignant tumors in the normal tissue and, malignancy and the like). Therefore, in prostate cancer in which tumors are distributed irregularly in the organ, an ordinary optical microscopy analysis and a molecular biological analysis are conventionally incompatible with the use of the same needle biopsy tissue.

According to the tissue dividing jig 100, it is possible to place a needle biopsy tissue in a shape conforming to the shape of a needle without bending or twisting the needle biopsy tissue, and the needle biopsy tissue can be divided into two fragments accurately from the central portion thereof. Thus, the respective fragments obtained after dividing the needle biopsy tissue can be used immediately as a sample for histologic examination and a different sample for a molecular biological test having spatial correspondence to the sample for histologic examination. Specifically, in addition to preparation of a formalin-fixed, paraffin embedded specimen from a biopsy specimen collected for diagnosis of prostate cancer or the like, a tissue for preparation of a frozen specimen for DNA analysis also can be divided from exactly the same biopsy specimen. Accordingly, with reference to the malignancy of a cancer lesion obtained from a light microscope specimen, it becomes possible to cut out a frozen specimen from the same site and to perform DNA analysis.

Furthermore, by marking the end portion of the needle biopsy tissue with an ink for tissues, it becomes possible to identify the direction of the tissue (collecting direction). The direction of the tissue is identified by performing the marking, and the position can be checked accurately at the time of light microscopic diagnosis and tissue collection for DNA analysis.

FIG. 4 is a schematic explanatory view illustrating a process of dividing a needle biopsy tissue using a tissue dividing jig 100. In prostate biopsy, a tissue fragment is collected by transperineal or transrectal needle biopsy. Accordingly, an elongated cylindrical fragment (for example, about 0.8 mm×20 mm, about 130 µL) is collected. Conventionally, an ordinary needle biopsy specimen is transferred to a cartridge in a state of being bent. In this state, it is not possible to divide the needle biopsy specimen into two fragments in the longitudinal direction (the direction along the biopsy needle). In contrast, the tissue placement portion 102 of the tissue dividing jig 100 of this example is in a shape of a valley-like recess. Thus, at the time of transferring the collected needle biopsy tissue from the biopsy needle 120, it is possible to maintain the three-dimensional structure of the needle biopsy tissue S not be shifted from the three-dimensional positions in the state when it was collected (FIGS. 4A and 4B).

In this state, the guide portion 107 and the cutting blade member 105 are disposed on the tissue dividing base 101. The guide portion 107 is disposed at a predetermined position on the tissue dividing base 101 by the positioning mechanism (see FIG. 2).

Figure 4A:
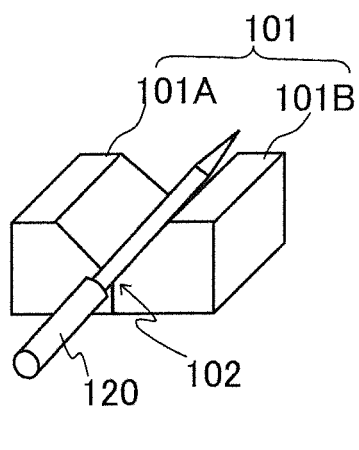
FIGS. 4A to 4D are schematic explanatory views illustrating a process of dividing a needle biopsy tissue using the tissue dividing jig 100.
Figure 4B:
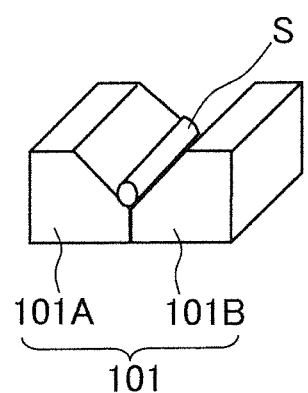
Figure 4C:
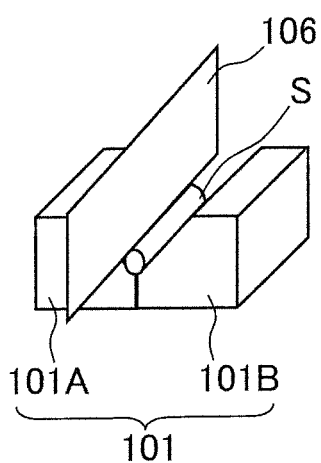

Next, by moving the cutting blade member 105 along the guide hole 108 of the positioned guide portion 107, the cutting blade 106 is lowered to reach the needle biopsy tissue S (see FIG. 3) and divides the needle biopsy tissue S. At this time, by disposing the cutting blade 106 to be placed at the center of the valley-like recess of the tissue placement portion 102, the needle biopsy tissue S placed on the tissue placement portion 102 can be divided into two fragments in the longitudinal direction (the direction along the biopsy needle) (FIG. 4C).

As shown in FIG. 3, it is preferable that a sheet-like member 109 having an affinity for the needle biopsy tissue S is placed on the tissue placement portion 102. As the sheet-like member 109, a filter paper, a pressure-sensitive adhesive sheet, a pressure-sensitive adhesive film, a nonwoven fabric sheet, or the like can be used suitably. As the filter paper, for example, it is possible to use a "Filter Paper for Uni-Cassette <Biopsy>6" (Sakura Finetek Japan Co., Ltd.) or the like, which is a filter paper suitable for needle biopsy specimens. By the sheet-like member 109, the needle biopsy tissue S is fixed by sticking action, and therefore, it becomes possible to perform cutting more accurately.

FIG. 5 is a schematic explanatory view illustrating a process of transferring a needle biopsy tissue S collected with the biopsy needle 120 to the tissue placement portion 102 (or the sheet-like member 109). FIG. 5A shows the biopsy needle 120. In the biopsy needle 120, a notch 121 is formed as a needle biopsy tissue collection portion. When the biopsy needle 120 is moved forward in a target tissue and then is taken out, the needle biopsy tissue S is held in the notch 121 as shown in FIG. 5B, whereby specimen collection can be achieved. The biopsy needle 120 thus taken out is disposed easily at a fixed position on the tissue placement portion 102 with the use of the tissue dividing jig 100 (FIG. 5C). Then, the needle biopsy tissue S is transferred to the tissue placement portion 102 by bringing the needle biopsy tissue S into contact with the tissue placement portion 102 (FIGS. 5D and 5E). At this time, if the sheet-like member 109 is placed on the tissue placement portion 102, the transfer can be carried out more suitably. Also, the transfer may be performed by providing a suction device in the tissue placement portion 102 and sucking the needle biopsy tissue S in the state shown in FIG. 5D. In this example, as the sheet-like member 109, a breathable material such as filter paper may be used.

It is preferable that the sheet-like member 109 can be divided by the cutting blade 106. When the sheet-like member 109 can be divided, needle biopsy tissues SA and SB obtained after dividing the needle biopsy tissue S into two fragments can be taken out easily from the tissue dividing jig 100 in the state where the needle biopsy tissues SA and SB are held integrally with the divided sheet-like members, respectively. This configuration is preferable because the three-dimensional structures of the needle biopsy tissues SA and SB obtained after the dividing can be prevented from being shifted from the three-dimensional positions in the state when they were collected, during the process of taking them out.

Also, it is preferable that a specific position of the sheet-like member 109 is provided with a mark that is orthogonal to the cutting direction, for example, because this allows the direction of the tissue (collecting direction) to be identified and also, the positional relationship between needle biopsy tissues obtained after cutting becomes comprehensible. With this configuration, at the time of light microscopic diagnosis and tissue collection for DNA analysis, the position can be checked more accurately. It is also preferable that a sample number and the like are printed on the sheet-like member 109.

Figure 4D:
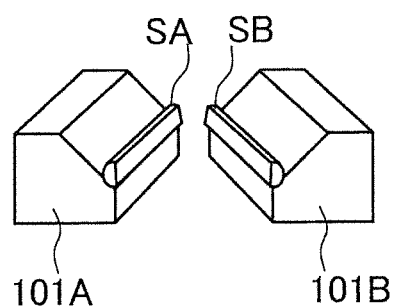
Figure 5A:
FIGS. 5A to 5E are schematic explanatory views illustrating a process of transferring a needle biopsy tissue S collected with a biopsy needle 120 to a tissue placement portion 102.
Figure 5B:
Figure 5C:
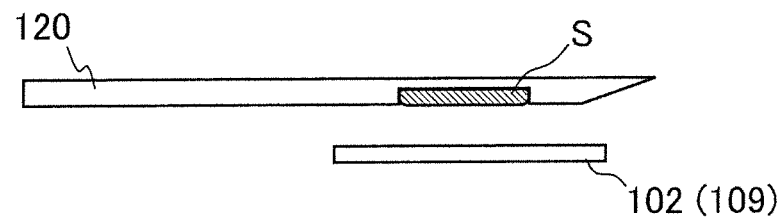
Figure 5D:
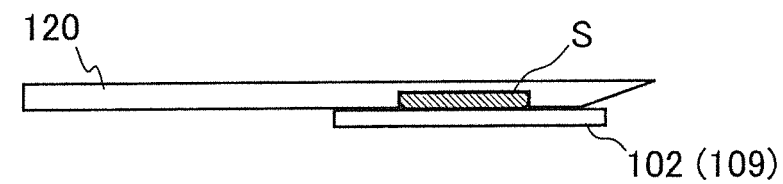
Figure 5E:
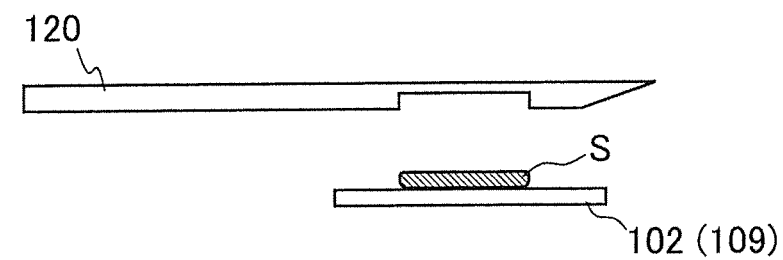

Furthermore, it is also preferable that, as shown in FIGS. 4A to 4D, the tissue dividing base 101 is composed of two members, namely, tissue dividing bases 101A and 101B, and can be divided at the cutting position of the needle biopsy tissue S. When the tissue dividing base 101 can be divided into the tissue dividing bases 101A and 101B at a position where the cutting blade 106 is in contact with the central portion of the recess, as shown in FIG. 4D, the respective needle biopsy tissues SA and SB obtained after dividing the needle biopsy tissue S into two fragments can be taken out easily from the tissue dividing jig 100 in the state where they are held integrally with the divided tissue dividing bases 101A and 101B, respectively. Alternatively, the tissue dividing base 101 may be formed of a single member, and the tissue dividing base 101 may be cut with the cutting blade 106 together with the needle biopsy tissue S. In this example, it is preferable that the tissue dividing base 101 is formed of a material that can be cut easily with the cutting blade 106.

The needle biopsy tissues SA and SB obtained by the dividing process described above have spatial correspondence over the entire lengths of the needle biopsy tissues SA and SB. By immersing one of the thus-divided needle biopsy tissues in formalin and quick-freezing the other one of the needle biopsy tissues, it is possible to obtain a fresh frozen fragment for DNA analysis and a permanent preparation embedded in paraffin or resin, which have spatial correspondence.

SECOND EXAMPLE

Figure 6:
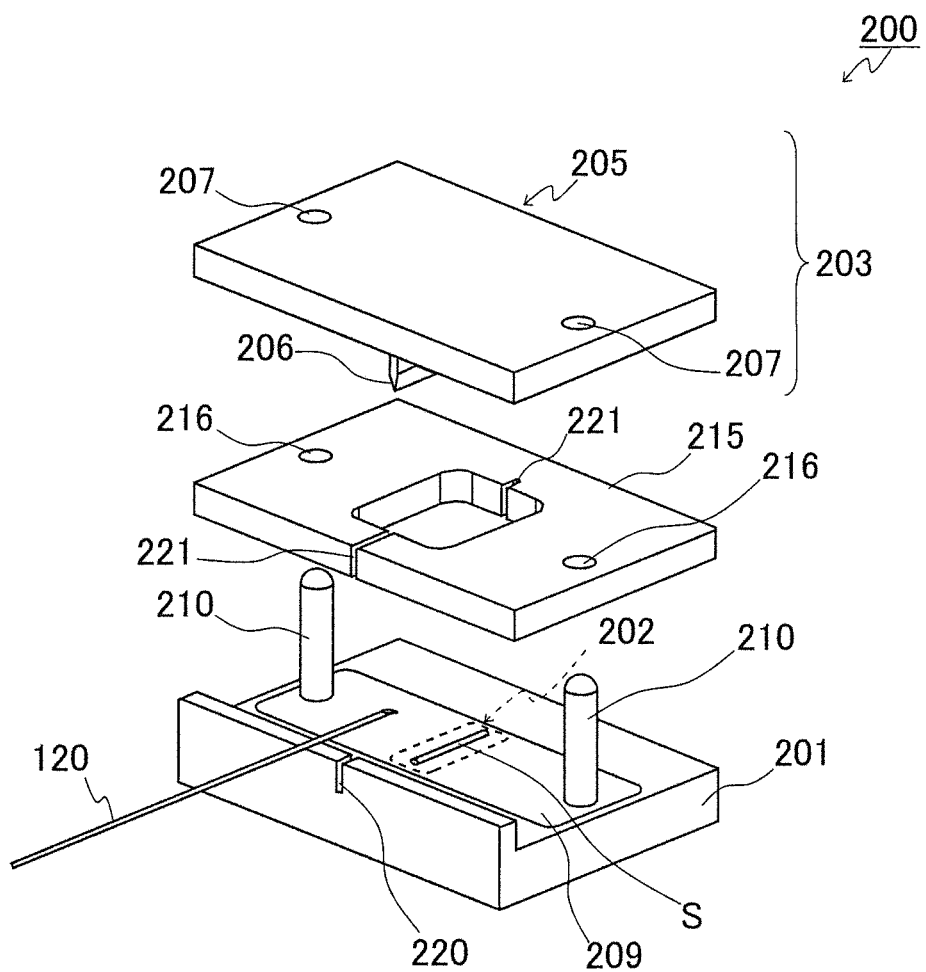
FIG. 6 is an exploded perspective view showing a tissue dividing jig 200 according to a second example.

FIG. 6 shows a tissue dividing jig 200 according to a second example. FIG. 6 is an exploded perspective view of a tissue dividing jig 200 in the state where a needle biopsy tissue S is taken out from a biopsy needle 120. The tissue dividing jig 200 has a tissue dividing base 201 and a cutting blade set 203. The tissue dividing base 201 has a tissue placement portion 202 on which the needle biopsy tissue S is to be placed. FIG. 6 shows the state where a sheet-like member 209 having an affinity for the needle biopsy tissue S is placed on the tissue placement portion 202. The cutting blade set 203 is provided with a cutting blade member 205 and guide portions 207. In this example, the guide portions 207 are formed integrally with the cutting blade member 205.

The tissue dividing base 201 and the cutting blade set 203 have a positioning mechanism for mutually fixing the positions thereof. The positioning mechanism in this example is composed of positioning pins 210 formed on the tissue dividing base 201 and the guide portions 207 formed on the cutting blade member 205. That is, the guide portions 207 function as positioning holes, and positioning of the tissue dividing base 201 and the cutting blade set 203 is achieved by inserting the positioning pins 210 into the guide portions 207 to combine them.

The cutting blade member 205 is provided with a cutting blade 206 that extends in the longitudinal direction of the tissue placement portion 202. The cutting blade 206 is disposed at a position where the cutting blade 206 divides the needle biopsy tissue S placed on the tissue placement portion 202 into two fragments in the longitudinal direction when the cutting blade set 203 is disposed at a predetermined position on the tissue dividing base 201 where the positions of the guide portions 207 coincide with the positions of the positioning pins 210, the positioning pins 210 are inserted into the guide portions 207, and the cutting blade set 203 is moved toward the tissue dividing base 201.

It is preferable that the tissue dividing jig 200 is provided with a biopsy needle guide 220. It is preferable to use the biopsy needle guide 220 because the needle biopsy tissue S can be placed easily at an appropriate position on the tissue dividing jig 200. Although the biopsy needle guide 220 for the biopsy needle 120 can be provided on the tissue dividing base 201 as shown in FIG. 6, this disclosure is not limited thereto.

Figure 7:
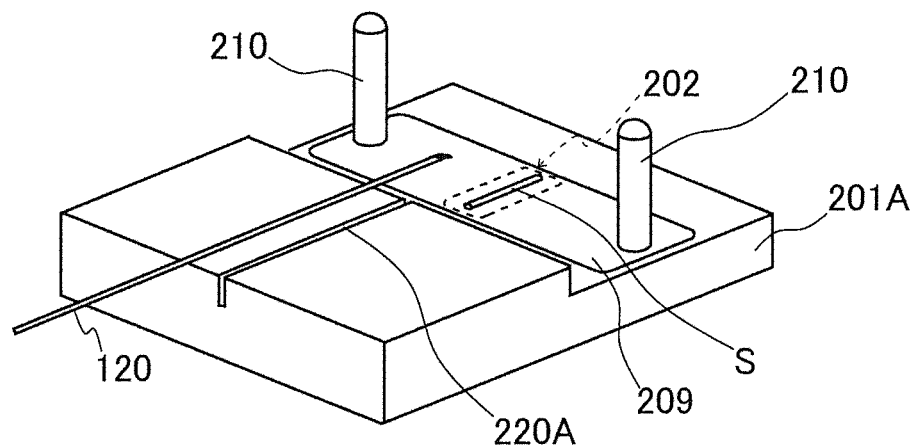
FIG. 7 is a perspective view showing a tissue dividing base 201A according to a modified example of the tissue dividing jig according to the second example.

FIG. 7 shows a perspective view of a tissue dividing base 201A according to a modified example of the tissue dividing jig of this example. In this modified example, a biopsy needle guide 220A provided in the tissue dividing base 201A is longer than the biopsy needle guide 220. By using the biopsy needle guide 220A, fixation of the biopsy needle 120 in the lengthwise direction can be achieved reliably. As a result, it is possible to suppress unintentional movement of the biopsy needle 120 and thus to place a needle biopsy tissue S at a predetermined position on the tissue placement portion 202 more reliably.

Figure 8:
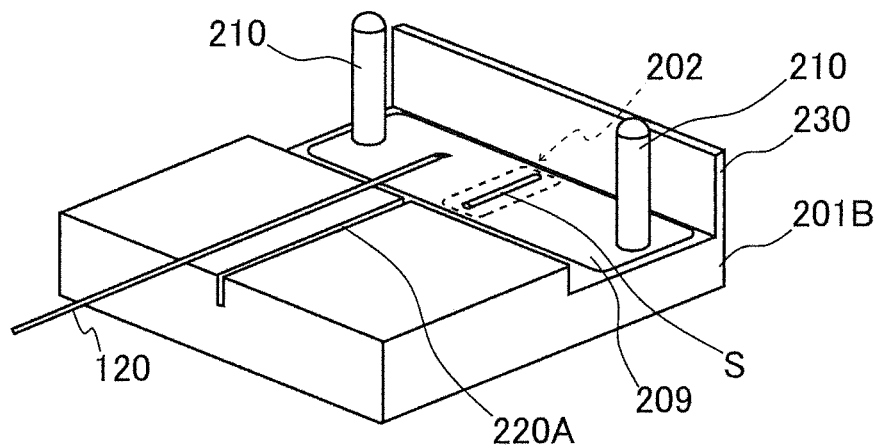
FIG. 8 is a perspective view showing a tissue dividing base 201B according to another modified example of the tissue dividing jig according to the second example.

Furthermore, FIG. 8 shows a perspective view of a tissue dividing base 201B according to another modified example of the tissue dividing jig of this example. In this modified example, the dividing base 201B has a biopsy needle stopper portion (biopsy needle stopper wall) 230 in the tip direction of a biopsy needle 120. With the biopsy needle stopper portion 230, it is possible to place a needle biopsy tissue S at a specific position on a tissue placement portion 202 by aligning the tip position of the biopsy needle 120. Although FIG. 8 shows the biopsy needle stopper portion 230 in the form of a wall formed integrally with the tissue dividing base 201B, the biopsy needle stopper portion 230 is not limited thereto. For example, the biopsy needle stopper portion and the tissue dividing base may be provided as separate members, and the biopsy needle stopper portion may be mounted on the tissue dividing base to be movable with respect to the tissue dividing base. According to this configuration, the position at which a needle biopsy tissue is to be placed can be set freely depending on the position of the notch in the biopsy needle or the length of the needle biopsy tissue.

In this example, it is also preferable to use a pressing member 215. The pressing member 215 is disposed between the tissue dividing base 201 and the cutting blade set 203. By using the pressing member 215, the sheet-like member 209 is held during the transfer and the cutting of the needle biopsy tissue S to prevent lifting and slippage of the sheet-like member 209, whereby the transfer and the cutting of the needle biopsy tissue S can be performed more smoothly. Furthermore, when the pressing member 215 also is provided with a biopsy needle guide 221, misalignment is less likely to occur when the needle biopsy tissue S is transferred from the biopsy needle 120 onto the tissue placement portion 202. It is preferable that the tip side of the biopsy needle in the tissue placement portion is also provided with a biopsy needle guide 221, because unintentional movement of the biopsy needle can be further suppressed and the biopsy needle guide 221 also can function as a biopsy needle stopper portion. In this example, by providing positioning holes 216 also in the pressing member 215 and disposing the pressing member 215 at a fixed position relative to the tissue dividing base, it becomes possible to place the needle biopsy tissue S at a predetermined position accurately. Therefore, by dividing the needle biopsy tissue S into two fragments reliably and easily over the entire length of the needle biopsy tissue S, it is possible to obtain divided tissues with spatial correspondence.

Although this example is directed to a structure where the needle biopsy tissue S is divided into two fragments over the entire length of the needle biopsy tissue S using one cutting blade 206, this disclosure is not limited thereto. As the cutting blade member 205, it is also possible to use a cutting blade member (not shown) provided with a plurality of cutting blades 206 arranged in parallel in the longitudinal direction of the tissue placement portion 202. By using the plurality of cutting blades 206, it is also possible to divide the needle biopsy tissue S into three or more fragments over the entire length of the needle biopsy tissue S. For example, by using two cutting blades, the needle biopsy tissue S can be divided into three fragments.

THIRD EXAMPLE

Figure 9:
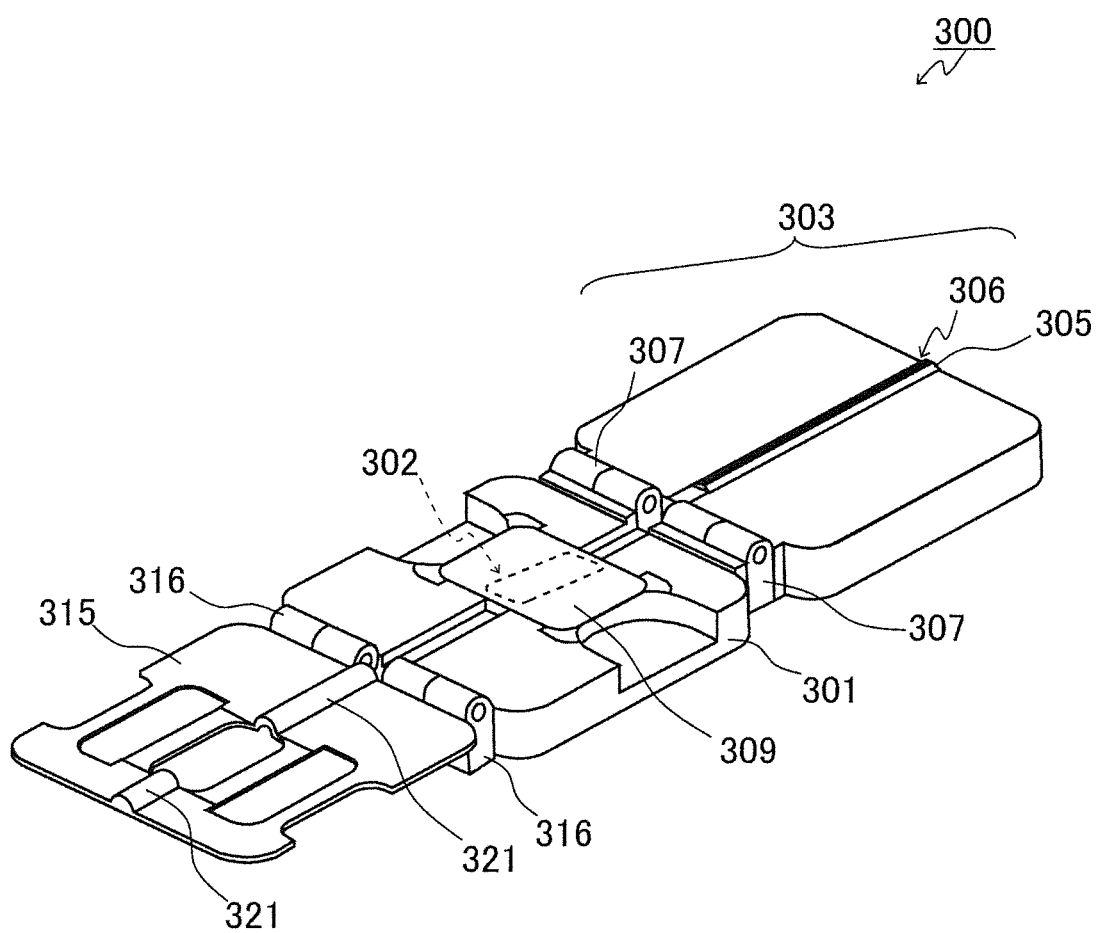
FIG. 9 is a perspective view showing a tissue dividing jig 300 according to a third example.

FIG. 9 shows a dividing jig 300 according to a third example. The tissue dividing jig 300 has a tissue dividing base 301 and a cutting blade set 303. The tissue dividing base 301 has a tissue placement portion 302 on which a needle biopsy tissue S is to be placed. FIG. 9 shows the state where a sheet-like member 309 having an affinity for the needle biopsy tissue S is placed on the tissue placement portion 302. The cutting blade set 303 is provided with a cutting blade member 305 and hinges 307.

The hinges 307 in this example correspond to the positioning mechanism and the guide portion. In this example, the hinges 307 join the cutting blade member 305 and the tissue dividing base 301 together to fix their positions mutually. Then, the cutting blade member 305 is guided by the hinges 307 to move to a fixed position on the tissue dividing base 301.

The cutting blade member 305 is provided with a cutting blade 306 that extends in the longitudinal direction of the tissue placement portion 302. The cutting blade 306 is disposed at a position where the cutting blade 306 divides the needle biopsy tissue S placed on the tissue placement portion 302 in the longitudinal direction when the cutting blade set 303 is disposed at a predetermined position on the tissue dividing base 301 by the hinges 307 and the cutting blade set 303 is moved toward the tissue dividing base 301.

In this example, it is also preferable to use a pressing member 315. The pressing member 315 is disposed between the tissue dividing base 301 and the cutting blade set 303. By using the pressing member 315, the sheet-like member 309 is held during the transfer and the cutting of the needle biopsy tissue S to prevent lifting and slippage of the sheet-like member 309, whereby the transfer and the cutting of the needle biopsy tissue S can be performed more smoothly. Furthermore, when the pressing member 315 also is provided with a biopsy needle guide 321, misalignment is less likely to occur when the needle biopsy tissue S is transferred from the biopsy needle 120 onto the tissue placement portion 302. It is preferable that the tip side of the biopsy needle in the tissue placement portion is also provided with a biopsy needle guide 321, because unintentional movement of the biopsy needle can be further suppressed and the biopsy needle guide 321 also can function as a biopsy needle stopper portion. In this example, it is preferable to join the pressing member 315 and the tissue dividing base 301 with hinges 316. According to this configuration, the pressing member 315 can be disposed at a fixed position relative to the tissue dividing base 301, and it becomes possible to place the needle biopsy tissue S at a predetermined position accurately. Therefore, by dividing the needle biopsy tissue S reliably and easily over the entire length of the needle biopsy tissue S, it is possible to obtain divided tissues with spatial correspondence.

Figure 10A:
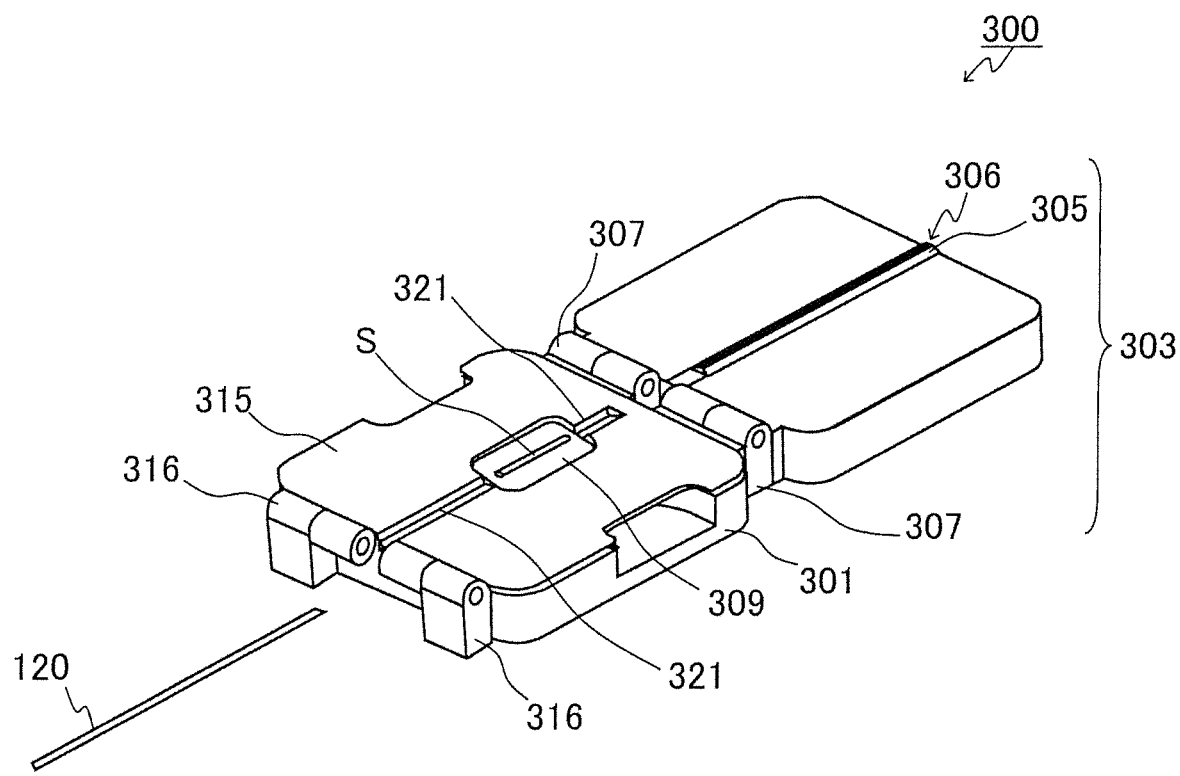
FIGS. 10A and 10B are perspective views showing the state of a tissue dividing jig 300 at the time of dividing a needle biopsy tissue.
Figure 10B:
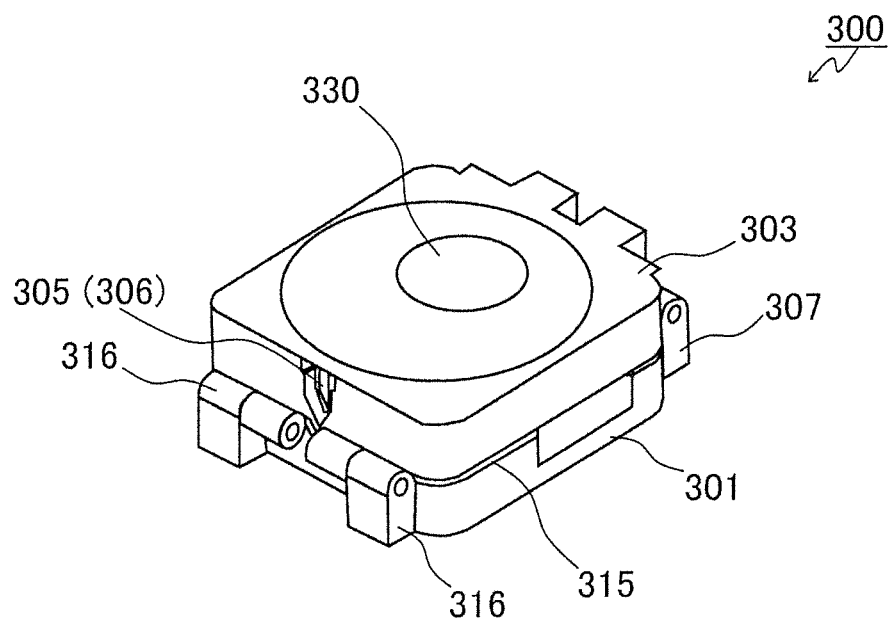

FIG. 10A is a perspective view showing the state of the tissue dividing jig 300 after the needle biopsy tissue S has been taken out from the biopsy needle 120. As shown in FIG. 10A, after the sheet-like member 309 is placed on the tissue placement portion 302, the pressing member 315 is disposed on the tissue dividing base 301. In this state, the biopsy needle 120 is inserted into the biopsy needle guide 321, and the needle biopsy tissue S is transferred by bringing the needle biopsy tissue S into contact with the sheet-like member 309. After transferring the needle biopsy tissue S, the biopsy needle 120 is removed from the biopsy needle guide 321, and the cutting blade set 303 is moved using the hinges 307. After moving the cutting blade set 303 to a predetermined position as shown in FIG. 10B, the cutting blade member 305 (cutting blade 306) is pushed into the needle biopsy tissue S to cut the needle biopsy tissue S. It is preferable that the cutting blade member is configured such that the cutting blade member 306 comes out when pushing the button 330 from the viewpoint of safety during operations. Furthermore, by using the cutting blade member 305 provided with a plurality of cutting blades 306, it is also possible to divide the needle biopsy tissue S into three or more fragments over the entire length of the needle biopsy tissue S.

When the sheet-like member 309 can be divided (cut) with the cutting blade 306 and the needle biopsy tissue is divided into three or more fragments using a plurality of cutting blades, a tissue located at a position other than end portions after the cutting (for example, when the needle biopsy tissue is divided into three fragments using two cutting blades, the divided needle biopsy tissue to be sandwiched between the cutting blades) and the sheet-like member may enter and remain in a space between the cutting blades. In this example, the needle biopsy tissue and the sheet-like member remaining in the space between the cutting blades are taken out using tweezers with thin tips or the like, for example. At this time, the operation has to be performed carefully to maintain the state of the tissue. Thus, to obtain divided tissues with spatial correspondence more easily, it is effective to provide non-cut regions in end portions of the sheet-like member 309, for example. When the sheet-like member 309 has the non-cut regions, the end portions of the sheet-like member 309 can be kept connected after the cutting, and therefore, it is possible to prevent the tissue and the sheet-like member after the cutting from entering and remaining in a space between the cutting blades.

Alternatively, by providing a step in each end portion of the tissue placement portion 302 on which the sheet-like member 309 is placed to prevent the sheet-like member 309 from being cut in the step portions even if the cutting blade 306 is pushed in, the end portions of the sheet-like member can be kept connected without being cut. Also, it is effective to use, as a cutting blade, a cutting blade having subjected to surface processing such as fluorine processing to allow the cutting blade and the needle biopsy tissue to be less likely to adhere to each other.

By using the tissue dividing jig, it is possible to divide a needle biopsy tissue easily into a plurality of fragments, namely, two fragments or three or more fragments, over the entire length of the needle biopsy tissue without using any special biopsy needle. As the biopsy needle, it is possible to use a commonly used biopsy needle. For example, "Bard MONOPTY (MAX•CORE) (trade name)" (Medicon Inc.), which is a disposable automatic biopsy needle or the like can be used.

As a specific example, our tissue dividing jigs have been described above with reference to examples where the tissue dividing jig is used to divide a needle biopsy tissue in prostate cancer. It is to be noted, however, that our tissue dividing jigs are not limited thereto. Our tissue dividing jigs are not only applicable to prostate cancer but also to cancer treatment of a wide region of other type of cancers and the like.

The invention claimed is:

1. A tissue dividing jig for dividing a needle biopsy tissue sample in a longitudinal direction corresponding to an axial direction along a biopsy needle,
   the tissue dividing jig comprising:
   a tissue dividing base comprising a tissue placement portion on which a sheet-like member is positioned,
   the sheet-like member having an affinity for the tissue sample,
   the sheet-like member configured to fix the tissue sample when the tissue sample is placed on the sheet-like member upon the placement portion;
   a cutting set attached to the dividing base by a first hinge on a first side of the dividing base,
   the cutting set provided with a cutting blade positioned halfway along a width of a largest face of a plate,
   the plate forming a backing of the cutting set,
   the cutting blade extending in the longitudinal direction;
   a pressing member attached to the dividing base by a second hinge on a second side of the dividing base,
   the second side being opposite the first side;
   and a biopsy needle guide comprising a groove and a stopping portion at an end of the groove,
   the groove positioned halfway along a width of a largest face of the pressing member;
   where the guide is configured to receive the biopsy needle and fix the biopsy needle in the longitudinal direction upon insertion of the biopsy needle into the guide;
   wherein the pressing member is configured to facilitate, via the stopping portion, a controlled transfer of the tissue sample onto the sheet-like member, the stopping portion being configured to reduce unintentional movement of the biopsy needle once the biopsy needle is inserted into the guide;
where the tissue dividing jig is configured to operate in a sequence of:
(1) the pressing member rotating along the second hinge to press down onto the sheet-like member,
(2) the sheet like member then fixing the tissue sample after the pressing member facilitates the controlled transfer of the tissue sample onto the sheet-like member,
then, (3) the cutting set rotating along the first hinge to move the cutting set along an arcuate path, whereupon the blade divides the tissue sample into two fragments in the longitudinal direction.

* * * * *